United States Patent [19]

Kulla et al.

[11] Patent Number: 5,187,093
[45] Date of Patent: * Feb. 16, 1993

[54] MICROORGANISMS USEFUL IN THE PROCESS FOR THE PRODUCTION OF L-CARNITINE

[75] Inventors: Hans Kulla, Visp; Pavel Lehky, Naters, both of Switzerland

[73] Assignee: Lonza Ltd., Gampel/Valais, Switzerland

[*] Notice: The portion of the term of this patent subsequent to Nov. 24, 2004 has been disclaimed.

[21] Appl. No.: 496,093

[22] Filed: Mar. 15, 1990

Related U.S. Application Data

[63] Continuation of Ser. No. 117,921, Nov. 6, 1987, abandoned, which is a continuation-in-part of Ser. No. 717,698, Mar. 29, 1985, abandoned.

[30] Foreign Application Priority Data

Mar. 29, 1984 [CH] Switzerland .................. 1600/84

[51] Int. Cl.$^5$ .................. C12N 1/12; C12N 1/20
[52] U.S. Cl. .................. 435/252.1; 435/128; 435/253.3; 435/824
[58] Field of Search .................. 435/128, 252.1, 253.3, 435/824

[56] References Cited

U.S. PATENT DOCUMENTS

| | | | |
|---|---|---|---|
| 2,313,573 | 3/1943 | Orthner et al. | 260/534 |
| 2,367,878 | 1/1945 | Lee | 260/482 |
| 3,466,364 | 9/1969 | Takahashi et al. | 424/70 |
| 3,711,549 | 1/1973 | Phillips et al. | 260/563R |
| 3,796,632 | 3/1974 | Fukumura | 435/824 |
| 4,371,618 | 2/1983 | Cavazza | 435/128 |
| 4,567,140 | 1/1986 | Voelskow et al. | 435/253.3 |
| 4,650,759 | 3/1987 | Yokzeki et al. | 435/128 |
| 4,708,936 | 11/1987 | Kulla et al. | 435/106 XR |
| 4,806,282 | 2/1989 | Tiuti et al. | 260/501.13 |

FOREIGN PATENT DOCUMENTS

| | | |
|---|---|---|
| 0122794 | 10/1984 | European Pat. Off. |
| 1903076 | 11/1969 | Fed. Rep. of Germany |
| 1939759 | 2/1970 | Fed. Rep. of Germany |
| 2751134 | 6/1979 | Fed. Rep. of Germany |
| 1198414 | 8/1970 | United Kingdom |

OTHER PUBLICATIONS

Miller, *Experiments in Molecular Genetics*, (1972), pp. 121-180.
Oraston et al., *Biochemical and Biophysical Research*, vol. 36, No. 1, (1969), pp. 179-184.
*Perry's Chemical Engineer's Handbook*, 6th Edition, (1984), p. 27-7.
Askens et al., J. Chem. Soc., pp. 103ff (1959).
Miller, J. H., "Experiments in Molecular Genetics", Cold Spring Laboratory, (1972), pp. 121 to 179.
Gerhardt, P. "Manual of Methods for General Bacteriology", Am. Soc. for Microbiology (1981), pp. 222 to 242.
Ornston, L. N., et al., Biochem. Biophys. Res. Commun. 35 (1969) pp. 179 to 184.
Vandecasteele, J. P., Applied Environ. Microbiol. 39, (1980), pp. 327 to 334.
Kulla H. G., et al., Arch. Microbiol. 135, (1983), pp. 1 to 7.
G. Lindstedt et al., Biochemisrty, 6, 1967, pp. 1262-1270.
G. Lindstedt et al., Biochemistry 16, 1977, pp. 2181-2188.
Seim et al., *Eur. Cong. Biotechnol.*, 3rd, vol. 1, 481-6 (1984).

*Primary Examiner*—Richard L. Raymond
*Attorney, Agent, or Firm*—Fisher, Christen & Sabol

[57] ABSTRACT

Process for the production of L-carnitine utilizing a microorganism. The microorganism is cultivated with crotonobetaine and/or γ-butyrobetaine in the presence of a growth substrate. The enriched L-carnitine is isolated. The microorganisms used are those which are capable of producing L-carnitine while not catabolizing it from crotonobetaine and/or γ-butyrobetaine. The microorganisms can be obtained by the following selection method. Microorganisms which grow with betaine, γ-butyrobetaine, crotonobetaine and L-carnitine as the C- and N-source are mutated in the conventional manner. From the culture obtained by cultivating of the mutated microorganisms, those microorganisms are selected which are stable, do not catabolize L-carnitine and do not grow on L-carnitine, crotonobetaine and γ-butyrobetaine, but grow with betaine.

3 Claims, No Drawings

MICROORGANISMS USEFUL IN THE PROCESS FOR THE PRODUCTION OF L-CARNITINE

This application is a continuation of application Ser. No. 117,921, filed on Nov. 6, 1987, now abandoned, which is a continuation-in-part of application Ser. No. 717,698, filed on Mar. 29, 1985, now abandoned.

BACKGROUND OF THE INVENTION

1. Field of the Invention

The invention relates to a process for the production of L-carnitine acid by biotechnical methods.

2. Prior Art or Related Art

The production of L-carnitine from γ-butyrobetaine is known. The γ-butyrobetaine is brought into contact with a hydroxylase-enzyme, liberated from spores of Neurospora crassa (U.S. Pat. No. 4,371,618), in the presence of sodium-2-oxoglutarate, a reducing agent, an iron ion source and a hydroxyl group donor solvent. Such process has the disadvantages of needing a multiplicity of co-factors. Thus, stoichiometric quantities of 2-oxoglutarate are decarboxylized oxidatively to succinate. $Fe^{2+}$ is needed as the $O_2$-activator, ascorbate is used in order to keep the iron in the reduced form, and catalase is needed to destroy the harmful $H_2O_2$.

Lindstedt et al., "The Formation and Degradation of Carnitine in Pseudomonas⇌ (Biochemistry 6, 1262-1270 (1967)), isolated a microorganism of the species Pseudomonas which grows with γ-butyrobetaine as a C- and N-source. The first reaction of the composition path was the hydroxylation of the γ-butyrobetaine to L-carnitine, whereupon the intermediately developing L-carnitine was further catabolized completely into $CO_2$, $H_2O$ and $NH_3$.

If such microorganism was used for the production of L-carnitine, such hydroxylase obtained from bacteria would also have the disadvantageous co-factor-requirements described by Lindstedt et al., "Purification and Properties of γ-Butytrobetaine Hydroxylase from Pseudomonas sp. AK 1", Biochemistry 16, 2181-2188, (1977).

BROAD DESCRIPTION OF THE INVENTION

An object of the invention is to provide a process which overcomes the above-stated disadvantages of the prior art and mentioned related art. Another object of the invention is to provide new microorganisms which do not have the disadvantages of the known microorganisms of the known processes and which would make it possible in a simple manner of not producing the racemate carnitine, but of producing enantio-selectively L-carnitine from crotonobetaine, butyrobetaine or mixtures thereof. A further object of the invention is to provide a process for obtaining the new microorganisms. Other objects and advantages are set out herein or are obvious herefrom to one skilled in the art.

The advantages and objects of the invention are achieved by the processes and microorganisms of the invention.

The invention includes microorganisms which are capable of producing L-carnitine from crotonobetaine and/or γ-butyrobetaine and do not catabolize the L-carnitine. Differing from the systems known the above-described prior art, the invention microorganisms use $H_2O$ and not the $O_2$, as hydroxyl group donor, as was determined by examinations using $H_2^{18}O$ and $^{18}O_2$.

Such microorganisms are live.

As a comparative examination of soil samples from four continents showed, the microorganisms which catabolize bytyrobetaine and crotonobetaine via L-carnitine are omnipresent. The isolation succeeds also from activated sludge of clarification plants. Potentially, all these strains come within the scope of the invention as L-carnitine producers, whenever they are mutated according to the principles of the invention stated below. Such mutants are obtainable by the following selection methods of the invention:

(a) Microorganisms, which grow with betaine, γ-butyrobetaine, crotonobetaine and L-carnitine as the C- and N-source, are mutated in the conventional or customary manner.

(b) From the culture obtained by cultivation of the mutated microorganisms, the mutated microorganisms are selected which are stable, do not catabolize L-carnitine and do not grow on L-carnitine, crotonobetaine or γ-butyrobetaine, but do grow with betaine.

Preferably, succeeding selection step (b), the microorganisms are selected which excrete L-carnitine and do not grow on L-carnitine, crotonobetaine or γ-butyrobetaine, but do grow with betaine.

Effectively, the mutated microorganisms are cultivated further in a betaine medium and these microorganisms which have been cultivated further are cultivated further preferably in an L-carnitine medium in order to carry out selection step (b). The cultivation of strains growing with betaine, γ-butyrobetaine, crotonobetaine and L-carnitine as a C- and N-source is carried out effectively in such a manner that one produces mixed cultures from mixtures of bacteria by inoculation of crotonobetaine nutritional solvents and that one starts from these, with the help of traditional microbiological techniques, pure cultures of microorganisms degrading crotonobetaine. The mutation of such a culture which grows with betaine, γ-butyrobetaine, crotonobetaine and L-carnitine as a C- and N-source can be carried out according to known methods. [J. H. Miller, "Experiments in Molecular Genetics", cold Spring Harbor Laboratory, (1972), pp. 121 to 180].

Methods usable effectively for the production of stable mutants are the frame-shift method, the deletion method and the transposon-insertion method. The microorganisms mutated in this way are then subjected to selection step (b), after further cultivation in a betaine medium and transfer in an L-carnitine medium whereby means of known "counter-selecting agents" [P. Gerhardt et al., (eds.), Manual of Methods for General Bacteriology, Am. Soc. for Microbiology, (1981), pp. 222 to 242] those microorganisms are selected which are stable, do not catabolize L-carnitine and do not grow on L-carnitine, crotonobetaine or γ-butyrobetaine, but do grow with betaine.

To produce L-carnitine according to the invention, live microorganisms themselves (not the enzymes released from treated spores or microorganisms) are used.

DETAILED DESCRIPTION OF THE INVENTION

As used herein, all parts, ratios, percentages and proportions are on a weight basis unless otherwise stated herein or otherwise obvious herefrom to one ordinarily skilled in the art.

A preferred microorganism which grows with betaine, γ-butyrobetaine, crotonobetaine and/or L-carnitine as C- and N-source is the strain HK 4 (DSM No. 2938)

and its descendants and mutants. The new strain DSM 2938 was deposited on Mar. 3, 1984 in the German collection of microorganisms (DSM), Gesellschaft fuer Biotechnologische Forschung mbH., Griesebachstrasse 8, 4300 Goettingen, Federal Republic of Germany, under the designation or number DSM 2938. Such deposit of a culture of such new strain of microorganism in such depository affords permanence of the deposit and ready accessibility thereto by the public if a patent is granted, under conditions which assure (a) that access to the culture will be available during the pendency of the patent application to one determined by the Commissioner to be entitled thereto under 37 C.R.R. 1.14 and 35 U.S.C. 122, and (b) that all restrictions on the availability to the public of the culture so deposited will be irrevocably removed upon the granting of the patent. The applicants or their assigns have provided assurance of permanent availability of the culture to the public through such depository.

The scientific (taxonomic) description of the strain (HK 4) DSM No. 2938 is as follows:

| Form of the cell | rods, partly pleomorphic |
|---|---|
| length μm | 1-2 |
| width μm | 0.5-0.8 |
| mobility | + |
| flagellata | peritric |
| gram-reaction | − |
| spores | − |
| formation of poly-β-hydroxybutyrate | − |
| oxidase | + |
| catalase | + |
| growth: | |
| anaerobe | − |
| 37° C. | + |
| 41° C. | − |
| pH 5.6 | − |
| Mac-Conkey-agar | + |
| SS-agar | − |
| cetrimide-agar | − |
| formation of pigment: | |
| non-diffusing | − |
| diffusing | − |
| fluorescent | − |
| formation of acid (OF-Test) from: | |
| glucose aerobe | − |
| anaerobe | − |
| fructose aerobe | − |
| ASS glucose | + |
| xylose | + |
| trehalose | + |
| ethanol | − |
| gas formation from glucose | − |
| ONPG | + |
| arginine dihydrolase | − |
| lysin decarboxylase | − |
| phenyl alanine deaminase | − |
| ornithine decarboxylase | − |
| H$_2$S | − |
| Vogas-Proskauer | − |
| indole | − |
| nitrite from nitrate | + |
| denitrification | + |
| formation of levan | − |
| lecithinase | − |
| urease | + |
| degradation of: | |
| starch | − |
| gelatin | − |
| casein | − |
| tyrosine | − |
| Tween 80 | − |
| DNA | + |
| aesculin | + |
| utilization of substrate: | |
| acetate | − |

-continued

| | |
|---|---|
| citrate | − |
| malonate | − |
| glycine | − |
| norleucin | − |
| xylose | + |
| fructose | + |
| glucose | + |
| autotrophic growth with H2 | − |
| 3-ketolactose | − |
| growth: | |
| betaine | + |
| L-carnitine | + |
| -butyrobetaine | + |
| crotonobetaine | + |

A preferred microorganism is a mutant of the previously described microorganism, which is stable, does not catabolize L-carnitine, but excretes, and does not grow on L-carnitine, crotonobetaine and γ-butyrobetaine, but does indeed grow on betaine, is the strain HK 13 (DSM No. 2903). The new strain DSM 2903 was deposited on Jan. 23, 1984, in the German collection of microorganisms (DSM), Gesellschaft fuer Biotechnologische Forschung mbH., Griesebachstrasse 8, 4300 Goettingen, Federal Republic of Germany, under the designation or number DSM 2903. Such deposit of a culture of such new strain of microorganism in such depository affords permanence of the deposit and ready accessibility thereto by the public if a patent is granted, under conditions which assure (a) that access to the culture will be available during the pendency of the patent application to one determined by the Commissioner to be entitled thereto, under 37 C.F.R. 1.14 and 35 U.S.C. 122, and (b) that all restrictions on the availability to the public of the culture so deposited will be irrevocably removed upon the granting of the patent. The applicants or their assigns have provided assurance of permanent availability of the culture to the public through such depository.

The scientific (taxonomic) description of the strain (HK 13) DSM No. 2903 is as follows:

| Form of the cell | rods partly pleomorphic |
|---|---|
| length μm | 1-2 |
| width μm | 0.5-0.8 |
| mobility | + |
| flagellata | peritric |
| gram-reaction | − |
| spores | − |
| formation of poly-β-hydroxybutyrate | − |
| oxidase | + |
| catalase | + |
| growth: | |
| anaerobe | − |
| 37° C. | + |
| 41° C. | − |
| pH 5.6 | − |
| Mac-Conkey-agar | + |
| SS-agar | − |
| cetrimide-agar | − |
| formation of pigment: | |
| not diffusing | − |
| diffusing | − |
| fluorescent | − |
| formation of acid (OF-Test) from: | |
| glucose aerobe | − |
| anaerobe | − |
| fructose aerobe | − |
| ASS glucose | + |
| xylose | + |

-continued

| | |
|---|---|
| trehalose | + |
| ethanol | − |
| formation of gas from glucose | − |
| ONPG | + |
| arginine dihydrolase | − |
| lysin decarboxylase | − |
| phenyl alanine deaminase | − |
| ornithine decarboxylase | − |
| $H_2S$ | − |
| Voges-Proskauer | − |
| indol | − |
| nitrite from nitrate | + |
| denitrification | + |
| formation of levan | − |
| lecithinase | − |
| urease | + |
| decomposition of: | |
| starch | − |
| gelatin | − |
| casein | − |
| tyrosine | − |
| Tween 80 | − |
| DNA | + |
| aesculin | + |
| utilization of substrate: | |
| acetate | − |
| citrate | − |
| malonate | − |
| norleucin | − |
| xylose | + |
| fructose | + |
| glucose | + |
| autotrophic growth with $H_2$ | − |
| 3-ketolactose | − |
| growth: | |
| betaine | + |
| L-carnitine | − |
| γ-butyrobetaine | − |
| crotonobetaine | − |
| L-glutamate and crotonobetaine | ± |
| L-glutamate and butyrobetaine | ± |
| L-glutamate and L-carnitine | ± |

An example of a descendant of the microorganism HK 13 (DSM No. 2903) which is stable, does not catabolize L-carnitine, but excretes it, does not grow on L-carnitine, crotonobetaine and γ-butyrobetaine, but does indeed grow with betaine, L-glutamate and crotonobetaine, L-glutamate and butyrobetaine, L-glutamate and L-carnitine, is the strain HK 1331 b (DSM No. 3225). It was isolated as a spontaneous, well growing mutant-colony from the surface of a nutrient medium solidified with agar, which contained L-glutamate and γ-butyrobetain. The new strain DSM 3225 was deposited on Feb. 8, 1985, in the German collection of microorganisms (DSM), Gesellschaft fuer Biotechnologische Forschung mbH., Griesebachstrasse 8, 4300 Goettingen, Federal Republic of Germany, under the designation or number DSM 3225. Such deposit of a culture of such new strain of microorganisms in such depository affords permanence of the deposit and ready accessibility thereto by the public if a patent is granted, under conditions which assure (a) that access to the culture will be available during the pendency of the patent application to one determined by the Commissioner to be entitled thereto under 37 C.F.R. 1.14 and 35 U.S.C. 122, and (b) that all restrictions on the availability to the public of the culture so deposited will be irrevocably removed upon the granting of the patent. The applicants or their assigns have provided assurance of permanent availability of the culture to the public through such depository.

The scientific (taxonomic) description of the achromobacter xylosoxydans strain (HK 1331 b) DSM No. 3225 is as follows:

| | |
|---|---|
| Form of the cell | rods partly pleomorphic |
| length μm | 1-2 |
| width μm | 0.5-0.8 |
| mobility | + |
| flagellata | peritric |
| gram-reaction | − |
| spores | − |
| formation of poly-β-hydroxybutyrate | − |
| oxidase | + |
| catalase | + |
| growth: | |
| anaerobe | − |
| 37° C. | + |
| 41° C. | − |
| pH 5.6 | − |
| Mac-Conkey-agar | + |
| SS-agar | − |
| cetrimide-agar | − |
| formation of pigment: | |
| not diffusing | − |
| diffusing | − |
| fluorescent | − |
| formation of acid (OF-Test) from: | |
| glucose aerobe | − |
| anaerobe | − |
| fructose aerobe | − |
| ASS glucose | + |
| xylose | + |
| trehalose | + |
| ethanol | − |
| gas formation from glucose | − |
| ONPG | + |
| arginine dihydrolase | − |
| lysin decarboxylase | − |
| phenyl alanine deaminase | − |
| ornithine decarboxylase | − |
| $H_2S$ | − |
| Voges-Proskauer | − |
| indol | − |
| nitrite from nitrate | + |
| denitrification | + |
| formation of levan | − |
| lecithinase | − |
| urease | + |
| decomposition of: | |
| starch | − |
| gelatin | − |
| casein | − |
| tyrosin | − |
| Tween 80 | − |
| DNA | + |
| aesculin | + |
| utilization of substrate | |
| acetate | − |
| citrate | − |
| malonate | − |
| glycine | − |
| norleucin | − |
| xylose | + |
| fructose | + |
| glucose | + |
| autotrophic growth with $H_2$ | − |
| 3-ketolactose | − |
| growth: | |
| betaine | + |
| L-carnitine | − |
| γ-butyrobetaine | − |
| crotonobetaine | − |
| L-glutamate and crotonobetaine | + |
| L-glutamate and | + |

| -continued | |
|---|---|
| butyrobetaine L-glutamate and L-carnitine | + |

The process for the production of L-carnitine can be carried out effectively in such a way that a preculture of a microorganism, preferably of a microorganism with the designation HK 13 (DSM 2903) is cultivated in a sterilized, preferably vitamin containing mineral medium [Kulla et al., Arch. Microbiol. 135, 1 to 7 (1983)] at 20° C. to 40° C., preferably at 30° C., at an effective pH value of 6 to 8, preferably 7, for 20 to 50 hours, preferably for 30 to 40 hours. This preculture contains effectively 0.1 to 10 percent by weight, preferably 0.5 to 5 percent by weight, of choline, glutamate, acetate, dimethylglycine or betaine as a growth substrate. Particularly preferred is betaine in quantity of 0.5 to 5 percent by weight.

Furthermore, it is customary with microbiology techniques to add to the preculture also the starting compounds that are to be converted—in this case, γ-butyrobetaine, crotonobetaine or mixture thereof in a quantity of 0.1 to 10 percent by weight, preferably 0.5 to 5 percent by weight, related to the reaction medium. The γ-butyrobetaine or crotonobetaine can be present as a hydrochloride salt or as a free inner salt as well as in the form of one of its derivatives.

Using the preculture produced according to the process mentioned above, further cultures can be inoculated. These further cultures have effectively the same composition as the precultures.

The crotonobetaine, γ-butyrobetaine or mixtures thereof that are to be converted are present in a concentration of 0.1 to 10 percent by weight, preferably 0.5 to 5 percent by weight. Also the growth substrate, choline glutamate, acetate, dimethylglycine and/or betaine, are used effectively in the concentrations used in the case of the preculture.

Advantageously, the cultivation conditions of the further cultivation are adapted corresponding to the cultivation conditions of the precultivation. Therefore, the temperatures effectively vary between 20° and 40° C., effectively vary between 20° and 40° C., most effectively at 30° C., and the pH value is kept as a rule between 6 to 8, advantageously at 7.

A production of L-carnitine carried out in this manner comes to a standstill after 20 to 30 hours. The concentration of L-carnitine is then equivalent to the quantity of γ-butyrobetaine or crotonobetaine as a rule. The cells can be centrifuged or filtered off and can be used as inoculation material for a new culture.

In a known manner [J. P. Vandecasteele, Appl. Environ. Microbiol. 39, 327 (1980) to 334, the L-carnitine can be brought out from the supernatant by means of cation exchanger chromatography and can be purified by recrystallization.

The invention process for the production of L-carnitine can also be carried out in a continuous manner by allowing the cells to grow in a chemostate at an effective dilution rate of 0.04 to 0.2 h$^{-1}$, preferably at 0.06 to 0.08 h$^{-1}$, at conditions analagous to those in the case of the batch culture.

By way of summary, the invention involves the production of L-carnitine from crotonobetaine and/or γ-butyrobetain by way of microbiology.

The pertinent parts of commonly-owned concurrently filed herewith application Ser. No. 717,546, now U. S. Pat. No. 4,708,936, entitled "Process For The Continuous Production Of L-Carnitine", by Hans Kulla, Pavel Lehky and Armand Squaratti are incorporated herein by reference.

The methods of applicants and U.S. Pat. No. 4,371,618 (Cavazza) differ substantially from each other and applicants' method is so clearly superior to that of Cavazza.

Since Cavazza filed its parent Italian patent application January 1980, assignee Sigma-Tau Undustrie Farmaceutiche has been unable to utilize such method for the production of L-carnitine. This is not surprising because the Cavazza method is believed to not work even on the laboratory scale. This is surely the reason why Cavazza did not present a single example of L-carnitine production by such method in such patent application.

On the other hand, since 1984 applicants' process has spaced from the laboratory scale to pilot-plant with a capacity of production of several tons of pure L-carnitine per year.

This evidences that applicants' process works and is highly suitable for the industrial production of L-carnitine.

In order to present clearly the differences between the methods of Cavazza and applicants, several of the most important properties of both methods are compared in following Table I.

TABLE I

COMPARISON OF CAVAZZA AND APPLICANTS' PROCESSES FOR THE PRODUCTION OF L-CARNITINE

| Cavazza | Applicants |
|---|---|
| 1. Completely different enzymes involved: | |
| γButyrobetainhydroxylase - one enzyme hydroxylates γButyrobetaine in a single, but very complex step. (See FIG. 1.) | L-carnitine is formed in a process similar to β-oxidation of fatty acids (Several different enzymes activities are required). (See FIG. 2.) |
| 2. Origin of O-atoms in hydroxyl of L-carnitine: | |
| O-atom comes from $O_2$ | O-atom comes from $H_2O$ |
| 3. Source of enzymes: | |
| Eukaryotic cell - Neurospora crassa | Procaryotic cells - deposited strains and other possible future isolates. |
| 4. Form of enzymes: | |
| Enzyme is isolated from spores. Isolation of enzyme requires isolation and opening of the spores and purification of enzyme. The enzyme is unstable even at −24° C., during the activity assay, already after 7 minutes a clear decrease of activity is observed. (Such an instability alone precludes an industrial use of this enzyme). (N.S. Punekar et al., J. Bid. Chem., (1987), 262, 6720-6724). | The enzymes of the pathway are localized inside the cell, where they are optimally protected against denaturation. In case of denaturation the enzymes are immediately replaced by newly synthetised enzyme-molecules in- |

TABLE I-continued
COMPARISON OF CAVAZZA AND APPLICANTS' PROCESSES FOR THE PRODUCTION OF L-CARNITINE

| Cavazza | Applicants |
|---|---|
| | side the living cells. Therefore it is not necessary to open the cells and release the enzyme. Cells with enzymes are easily separated from the culture medium. |
| 5. Cofactors: | |
| Several cofactors (in equimolar amounts) are necessary for the synthesis of L-carnitine: 2-oxoglutaric acid, ascorbic acid, catalase, ferrous ions. | No cofactors (with exception of betain and the usual trace elements) are required for the production of L-carnitine. |
| The price of all these cofactors exceeds the price of L-carnitine produced by other methods (isolation of pure L-carnitine from such a mixture is difficult). | Since only L-carnitine and less than 10 percent of γ-butyrobetaine are present in the medium, isolation of L-carnitine is trivial. |
| 6. Complexity of the process: | |
| Many steps are required: | Applicants' method is much more efficient: |
| (1) Growth of Neurospora biomass | (1) Growth of biomass is coupled with production of L-carnitine |
| (2) Sporulation | |
| (3) Isolation of spores | |
| (4) Opening of spores and isolation of enzyme | |
| (5) Preparation of cofactors | |
| (6) Production of L-carnitine | |
| (7) Separation of equimolar amounts of used cofactors | (2) Absence of cofactors allows us to isolate L-carnitine directly from the culture filtrate by separation of water. |
| (8) Isolation of L-carnitine | |
| 7. Economical aspects: | |
| According to applicants' experience the Cavazza process is not economically viable: Many production steps are required Requirement of expensive cofactors Necessity of elimination for used cofactors (succinate) before the isolation of L-carnitine The high cost of the enzyme is even further increased through the very high instability of γ-Butyrobetaine hydroxylase Pollution problems with iron and sulfites | Only two steps' required No cofactors Culture filtrate can be used directly for isolation of pure L-carnitine No enzyme isolation, constant intracellular level of enzyme is maintained by cells. |

As used herein, the phrase "a biologically pure culture" may include a slightly-contaminated culture, as such cultures are also productive (useful). To be biologically effective, slight contamination can be present in the culture of live microorganisms.

The practical use of the invention is illustrated by the following examples.

EXAMPLE 1

Isolation of a Microorganism Decomposing Crotonobetaine:

Microorganisms were extracted from soil using neutral phosphate buffer solution by stirring. Larger components were subsequently separated through filter paper. A crotonobetaine nutrient solution was inoculated with the bacteria mixture obtained in this way up to a slight cloudiness. After 9 days, the cloudiness had risen to ninety-fold as a measure of the cell concentration. Crotonobetaine has disappeared completely from the solution and ammonium was proven to exist as a degradation product. From the mixed culture and with the help of traditional microbiological techniques (solidified agar culture media), pure cultures of microorganisms decomposing crotonobetaine were started. A culture was selected for further work and was named HK 4 (DSM 2938). This strain also grew with γ-butyrobetaine, L-carnitine and betaine.

EXAMPLE 2

Isolation Of A Stable Carnitine Dehydrogenase Negative Mutant:

A stable carnitine dehydrogenase negative mutant should not be able to further catabolize L-carnitine built up from γ-butyrobetaine or crotonobetaine and, instead it should excrete in the ideal case. A culture of strain HK 4 (DSM 2938) was stably mutagenized with "acridin mutagen ICR 191", 5 microgram per ml, in a succinate medium as prescribed [J. H. Miller, Experiments in Molecular Genetics, Cold Spring Harbor Laboratory, 1972, pp. 121 to 179]. After that the cells according to standard were allowed to grow in a "nutrient broth" for the expression of the mutation. Then the culture was transferred into a betaine medium. A L-carnitine medium was inoculated with the fully grown culture. After a few hours, the culture reached logarithmic growth. At this point in time, penicillin G (15 mg/ml) and D-cycloserin (0.5 mg/ml) were added [Ornston et al., Biochim. Biophys. Res. Commun. 36, 179 (1969) to 184,]. These "counterselecting" agents kill only growing bacteria. The mutants, which can no longer grow with L-carnitine and in which the invention is interested, survived and enriched themselves relatively according to it. After 30 hours, the number of live cells was reduced to a factor of hundred—the antibiotica were washed away and the culture was transferred into a betaine-medium. After growth, corresponding dilutions of the culture were distributed on solidified nutritional agar. The cells isolated in such a way grew into colonies and were examined individually. The mutant HK 13 (DSM 2903) was selected. Stably, it had no carnitine-dehydrogenase and correspondingly no longer grew with L-carnitine, γ-butyrobetaine or crotonobetaine, but it indeed did with betaine. In the case of growth on betaine, dimethylglycine, choline, glutamate or acetate, this strain converted crotonobetaine or γ-butyrobetaine into L-carnitine and excreted it.

EXAMPLE 3

A 5-1 preculture of strain HK 13 (DSM 2903) was cultivated in a vitamin-containing mineral medium [Kulla et al., Arch. Microbiol. 135, 1 to 7 (1983)], which contained 1 percent by weight of betaine and 0.5 percent by weight of crotonbetaine-chloride, for 33 hours at 30° C. and pH 7.0. With this, a culture of 15 l of the same composition was inculated and just like the preculture (30° C., pH 7.0, $pO_2$ = 3 ppm) was cultivated for 24 hours. When the production came to a standstill, the cells were centrifuged away and were used as inculation material for a new batch. The concentration of L-carnitive was measured in the supernatant (19.8 l) by way of enzymatic analysis. The excess contained 4.26 mg of L-carnitine per ml. This corresponded to a yield of 95.0 percent, calculated on the quantity of crotonobetaine-chloride used. Educts or other impurities were not found to exist in the NMR spectrum. Using the method described in J. P. Vandecasteele, Appl. environ. Microbiol. 39, 327 to 334, (1989), the L-carnitine was brought out by means of cation exchanger chromatography from the supernatant and was purified by recrystallization.

EXAMPLE 4

A 5-1 preculture of strain HK 13 (DSM 2903) was cultivated in a vitamin-containing medium (according to Example 1), which contained 1 percent of choline and 0.6 percent of γ-butyrobetaine-chloride, at pH 7.0 and 30° C. for 32 hours. With this preculture, a culture of 15 l of medium of the same composition was inoculated and was cultivated under the same conditions as in Example 1. When the production came to a standstill after about 30 hours, the cells were separated by microfiltration (Amicon Hollow-fiber cartridge). This cell mass was used for the further production of L-carnitine. The concentration of L-carnitine was enzymatically determined in the filtrate (19.6 l). The filtrate contained 5.3 mg of L-carnitine per ml. This corresponded to an analytical yield of 97.6 percent, calculated on the quantity of γ-butyrobetaine-chloride used. According to the NMR analysis, no educts or other foreign organic by-products could be proven to exist in the filtrate. Therefore, the L-carnitine was isolated from the solution in a known manner, for example, by means of azeotropic distillation (German Patent No. 2,300,492).

EXAMPLE 5

A fermentor equipped for continuous culture which contained 1.5 l of a vitamin containing mineral medium (according to Example 1) with 1.5 percent of betaine and 1.0 percent of γ-butyrobetaine-chloride was inoculated with 150 ml of strain 13 (DSM 2903) preculture of the same medium. After 20 hours of aerobic cultivation at 30° C. and pH 7.0, the culture had grown up and the continuous operation was started at a flow rate of 0.1 l/h. The culture solution flowing out of the fermentor was caught in a vessel cooled at 4° C. the cells were removed by centrifugation. According to enzymatic analysis, the supernatant contained 8.8 g of L-carnitine per 1 of culture. This corresponded to a yield of 99.2 percent (proven analytically), calculated on the concentration of the γ-butyrobetaine-chloride used. The solid L-carnitine chloride was isolated from the solution by means of ion chromatography and water separation.

EXAMPLE 6

Example 4 was repeated using strain HK 1331 b (DSM 3225), whereby choline was substituted for 0.3 percent betaine plus 0.3 percent L-glutamate.

What is claimed is:
1. A biologically pure culture of live microorganism HK 13 (DSM No. 2903).
2. A biologically pure culture of live microorganism HK 1331 b (DSM No. 3225).
3. A biologically pure culture of live microorganism HK 4 (DSM No. 2938).

* * * * *